United States Patent [19]
Kelly

[11] Patent Number: 5,261,422
[45] Date of Patent: Nov. 16, 1993

[54] ACOUSTIC ADMINISTRATION OF REMEDIES PROCESS AND DEVICE

[76] Inventor: Michael P. Kelly, 3813 France Ave. South, Minneapolis, Minn. 55416

[21] Appl. No.: 784,526

[22] Filed: Oct. 29, 1991

[51] Int. Cl.$^5$ .................... A61B 19/00; A61H 39/02
[52] U.S. Cl. .................................. 128/898; 128/735; 128/907
[58] Field of Search ............ 128/897, 898, 907, 420.5, 128/746, 735

[56] References Cited

U.S. PATENT DOCUMENTS

| | | | |
|---|---|---|---|
| 4,073,296 | 7/1983 | McCall | 128/60 X |
| 4,408,617 | 10/1983 | Auguste | 128/907 X |
| 4,556,064 | 12/1985 | Pomeranz et al. | 128/907 X |
| 4,750,208 | 6/1988 | Yamada et al. | 128/33 X |
| 4,753,225 | 6/1988 | Vögel | 128/33 |
| 4,895,149 | 1/1990 | Morez | 128/907 X |
| 5,012,816 | 5/1991 | Lederer | 128/907 X |

OTHER PUBLICATIONS

"Occidental Institute Research Foundation Recommended Instrumentation," pp. 1–22.
"Working With the Rathera," pp. 1–26.

*Primary Examiner*—Randall L. Green
*Assistant Examiner*—Elizabeth M. Burke
*Attorney, Agent, or Firm*—Kinney & Lange

[57] ABSTRACT

The present invention provides a process and device for the administration of a remedy of a disease by sound waves. The sound waves are of a frequency and amplitude which correspond to the frequency and the amplitude of electro-magnetic oscillations given off by the remedy for the disease.

10 Claims, No Drawings

ACOUSTIC ADMINISTRATION OF REMEDIES PROCESS AND DEVICE

BACKGROUND OF THE INVENTION

The present invention relates to the treatment of diseases and more particularly to the use of sound waves of a certain frequency and amplitude to administer a remedy for disease treatment. The frequency and amplitude of the sound waves correspond to the frequency and amplitude of the electro-magnetic oscillations given off by the remedy.

The treatment of a diagnosed disease is an art which has been practiced throughout the history of man. Thousands of different remedies have been administered in many different ways. Medical science in the twentieth century has taught that selected pharmaceutical remedies (i.e. drugs) can chemically counteract the effects of almost any disease. Conventional drugs generally produce a predictable effect on the diseased organ or on the disease-causing pathogen. It is often not known exactly how the drug works within the body, just that the drug has a predictable effect.

Homeopathic medicine, widely practiced in foreign countries, approaches disease treatment from a different perspective. Homeopathic medicine uses the principal that the body has natural disease-fighting mechanisms, which can be properly stimulated to themselves combat a disease. Homeopathic remedies are substances found in nature which stimulate the body's own disease-fighting mechanisms. Rather than have a foreign drug fight the disease within the body, the homeopathic remedy aids the body's own disease-fighting chemistry in fighting the disease.

Homeopathic remedies, when taken in a large dosage, often have the capacity to produce the same symptoms as the disease. Introduction of a minute dosage can alert the body's disease-fighting mechanisms to the presence of a disease and focus the disease-fighting mechanisms toward fighting the disease.

Recently it has been theorized that the effectiveness of some medicines is related to the electro-magnetic oscillations or waves given off by the medicines. This is thought to be particularly true with homeopathic remedies. A homeopathic remedy gives off electro-magnetic oscillations of a particular frequency and amplitude, and the oscillations stimulate the body's natural disease-fighting chemistry to combat the disease.

Equipment has been designed to produce an electronic signal having a frequency and amplitude which corresponds to the electro-magnetic oscillations given off by a remedy. The electronic signal is then transmitted to the body of the patient. This practice is known as electro-acupuncture according to Vols ("EAV"). Examples of EAV equipment are the German "MORA-Therapy Unit", and the Dutch "Rathera" or "Myosun". EAV equipment works under the theory that the body's disease-fighting chemistry is affected by the frequency and amplitude of electronic signals similar to the way it is affected by the frequency and amplitude of electro-magnetic oscillations.

Conventional and homeopathic remedies have several major disadvantages. Traditional administration of a remedy requires consumption of the remedy by the user. Significant costs can be involved in purchasing an original prescription. Consumption of the remedy means that even more significant costs can be involved in purchasing subsequent refills. The remedy used may produce deleterious side effects, and the side effects may require remedies of their own. EAV equipment requires the patient to be in electrical contact with the equipment, also involving significant costs such as the cost of purchasing the equipment or visiting a practitioner.

SUMMARY OF THE INVENTION

The present invention uses sound waves to stimulate the body's own natural disease-fighting mechanisms. The electro-magnetic oscillations of a remedy are received and converted into an electronic signal. The electronic signal has a frequency and amplitude which corresponds to the frequency and amplitude of the electro-magnetic oscillations. The electronic signal is then connected to a speaker to produce sound waves. The sound waves have a frequency and amplitude which likewise corresponds to the frequency and amplitude of the electro-magnetic oscillations. The sound waves contact the body of the patient at a treatment effective intensity such that the frequency and amplitude of the oscillations given off by the remedy affect the body's natural disease-fighting chemistry.

The electronic signal of the present invention can be stored on a recording medium, which allows for easy transportation of the remedy. The recording medium can then be played on conventional playback devices to create the sound waves. The process and device of the present invention allows treatment of a disease at a one-time minimal cost, without consumption of the remedy. The sound waves can be repeatedly recreated, and the substantial cost of prescription refills is avoided. The process and device of the present invention can also avoid the deleterious side effects which can be caused by conventional remedies.

DETAILED DESCRIPTION OF THE PREFERRED EMBODIMENTS

The patient must first be independently diagnosed for a disease. A remedy may then be provided to generate electro-magnetic oscillations of a particular frequency and amplitude. The remedy may be provided in solid form without a container or in liquid form in glass capsules. The remedy may be placed in a brass beaker which serves as an antenna to receive the electro-magnetic oscillations of the remedy.

The electro-magnetic oscillations of the remedy may be converted into an electronic signal using prior art devices which are designed for this purpose, known as electro-acupuncture by Vols ("EAV") equipment. Examples include the "MORA Therapy Unit", and the "Rathera" or "Myosun". This EAV equipment can filter high or low frequencies out of the resulting electronic signal, amplify the intensity of the electronic signal, and intermit the electronic signal with pauses. A treatment session may include several different frequency filtration phases.

The electronic signal is attached to a speaker to generate sound waves having a frequency and amplitude which corresponds to the frequency and amplitude of the electro-magnetic oscillations of the remedy. The sound waves should contact a patient for a duration sufficient to effect an improvement. This duration will be between 5 and 20 minutes for most applications, but can be nearly instantaneous for certain patients and certain diseases.

The electronic signal may be recorded on any type of sound recording medium. The sound recording medium may be a magnetic tape such as a conventional cassette tape. The sound recording medium can then be easily transported and replayed on playback devices. The magnetic cassette tape may be replayed on any conventional cassette tape player.

The sound waves of the present invention produce vibrations within the body of the patient having a particular frequency and amplitude. It is believed that the frequency and amplitude of the sound waves affect the patient's natural disease-fighting chemistry. It is believed that the patient's natural disease-fighting chemistry is stimulated to better focus itself toward fighting the disease.

EXAMPLE 1

The present invention was used in preparing a Herpes treatment tape. The homeopathic remedies included: Herpes Nosode, Tonical Injel, Ubichonon, CoEmzym, Silymarin, Nero Injel, Hepar Compositum, Reneel, and Cerebrum Compositum. These homeopathic remedies generate electro-magnetic oscillations for the treatment of Herpes. The remedies were placed in a brass beaker which served as an antenna to receive the electro-magnetic oscillations given off by the remedy. The electro-magnetic oscillations were converted into an electronic signal having a corresponding frequency and amplitude.

A herpes treatment tape was made having five phases of frequency filtration, each phase including a number of cycles of intermittent sound. Each cycle consisted of five seconds of signal followed by three seconds of pause. Phase 1 included 28 cycles of sound in which frequencies more than 100 Hz were filtered out. Phase 2 included 16 cycles of sound in which frequencies of more than 200 Hz were filtered out. Phase 3 included 10 cycles of sound in which frequencies of more than 1,000 Hz Were filtered out. Phase 4 included 10 cycles of sound in Which frequencies of less than 1,000 Hz were filtered out. Phase 5 included 8 cycles of sound in which frequencies of less than 10,000 Hz were filtered out.

The herpes treatment tape was used on six patients who had recurrent Herpes Simplex outbreaks and who had each experienced outbreaks for several years prior to receiving treatment by acoustic administration. Four of these six patients were cured beyond a level of detection. The remaining two patients showed great suppression of the Herpes Simplex virus.

Although the present invention has been described with reference to preferred embodiments, workers skilled in the art will recognize that changes may be made in form and detail without departing from the spirit and scope of the invention.

What is claimed is:

1. A process for treatment of disease comprising the steps of:
   receiving electro-magnetic oscillations from a remedy for a disease, said remedy producing electro-magnetic oscillations;
   converting the electro-magnetic oscillations of the remedy into an electronic signal which corresponds to the electro-magnetic oscillations both in frequency and in amplitude;
   transmitting the electronic signal to a speaker thereby driving the speaker to produce sound waves which correspond to the electronic signal both in frequency and in amplitude; and
   contacting a patient having the disease with the sound waves at a treatment effective intensity.

2. The process of claim 1 wherein the step of receiving electro-magnetic oscillations comprises the step of:
   receiving electro-magnetic oscillations produced by a homeopathic remedy for a disease.

3. The process of claim 2 wherein the step of contacting a patient having the disease with the sound waves comprises the step of;
   contacting a patient having the disease and having a natural disease-fighting chemistry with the sound waves at an intensity such that the patient's natural disease-fighting chemistry is stimulated to better fight the disease.

4. The process of claim 1 wherein the step of transmitting the electronic signal to a speaker comprises the steps of;
   recording the electronic signal on a recording medium, and
   playing the recording medium to recreate the electronic signal.

5. The process of claim 4 wherein the step of recording the electronic signal on a recording medium comprises the step of:
   recording the electronic signal on a magnetic audio tape.

6. The process of claim 1 wherein the step of converting the electro-magnetic oscillations of the remedy into an electronic signal comprises the step of:
   filtering the electronic signal to eliminate selected frequencies.

7. The process of claim 1 wherein the step of contacting a patient having the disease with the sound waves continues for at least one session having a duration sufficient to effect an improvement.

8. The process of claim 7 wherein a plurality of sessions are performed on different days.

9. The process of claim 1 wherein the step of receiving electro-magnetic oscillations comprises the step of:
   receiving electro-magnetic oscillations from at least one member from the group consisting of:
   Herpes Nosode, Tonical Injel, Ubichonon, CoEmzym, Silymarin, Nero Injel, Hepar Compositum, Reneel, and Cerebrum Compositum, these members being homeopathic remedies for herpes.

10. A process for the treatment of disease comprising the steps of:
    receiving electro-magnetic oscillations from a homeopathic remedy for herpes, said homeopathic remedy producing electro-magnetic oscillations, wherein the homeopathic remedy is at least one member from the group consisting of:
    Herpes Nosode, Tonical Injel, ubichonon, CoEmzym, Silymarin, Nero Injel, Hepar Compositum, Reneel, and Cerebrum Compositum, these members being homeopathic remedies for herpes;
    converting the electro-magnetic oscillations of the homeopathic remedy into an electronic signal which corresponds to the electro-magnetic oscillations both in frequency and in amplitude;
    filtering the electronic signal to eliminate selected frequencies;
    recording the electronic signal on a magnetic audio tape;
    playing the magnetic audio tape to recreate the electronic signal;
    transmitting the electronic signal to a speaker thereby driving the speaker to produce sound waves which correspond to the electronic signal both in frequency and in amplitude; and contacting a patient having herpes and having a natural disease-fighting chemistry with the sound waves at a treatment effective intensity such that the patient's natural disease-fighting chemistry is stimulated to better fight herpes, wherein the sound waves contact the patient for a plurality of sessions each having a duration sufficient to effect an improvement.

* * * * *

UNITED STATES PATENT AND TRADEMARK OFFICE
CERTIFICATE OF CORRECTION

PATENT NO. : 5,261,422

DATED : November 16, 1993

INVENTOR(S) : Michael P. Kelly

It is certified that error appears in the above-indentified patent and that said Letters Patent is hereby corrected as shown below:

Column 4, line 53, delete "ubichonon" insert --Ubichonon--.

Signed and Sealed this

Thirty-first Day of May, 1994

Attest:

BRUCE LEHMAN

*Attesting Officer*  *Commissioner of Patents and Trademarks*